(12) United States Patent
Fischer et al.

(10) Patent No.: US 9,506,918 B2
(45) Date of Patent: Nov. 29, 2016

(54) METHODS OF SPECIFICALLY RELEASING A SUB-GROUP OF OBJECTS

(71) Applicant: Roche Diagnostics Operations, Inc., Indianapolis, IN (US)

(72) Inventors: Thomas Fischer, Munich (DE); Thomas Froehlich, Penzberg (DE); Dieter Hendl, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/673,049

(22) Filed: Mar. 30, 2015

(65) Prior Publication Data

US 2015/0204863 A1 Jul. 23, 2015

Related U.S. Application Data

(63) Continuation of application No. PCT/EP2013/070436, filed on Oct. 1, 2013.

(30) Foreign Application Priority Data

Oct. 2, 2012 (EP) .................... 12006876

(51) Int. Cl.
 *G01N 33/543* (2006.01)
 *G01N 33/50* (2006.01)
 *C12Q 1/68* (2006.01)

(52) U.S. Cl.
 CPC ....... *G01N 33/54306* (2013.01); *C12Q 1/6823* (2013.01); *C12Q 1/6834* (2013.01); *G01N 33/5005* (2013.01); *G01N 2800/00* (2013.01)

(58) Field of Classification Search
 CPC .......... G01N 33/50; G01N 33/54306; G01N 2800/00; C12Q 1/6834; C12Q 1/6823
 See application file for complete search history.

(56) References Cited

U.S. PATENT DOCUMENTS

| 5,622,929 A | 4/1997 | Willner et al. |
| 6,322,980 B1 | 11/2001 | Singh |
| 6,514,700 B1 | 2/2003 | Singh |
| 2005/0079565 A1 | 4/2005 | Chan-Hui et al. |
| 2006/0204999 A1 | 9/2006 | MacEvicz |

FOREIGN PATENT DOCUMENTS

| WO | 00/66607 A1 | 11/2000 |
| WO | 01/83502 A1 | 11/2001 |
| WO | 02/095356 A2 | 11/2002 |
| WO | 03/006947 A2 | 1/2003 |
| WO | 2005/072507 A2 | 8/2005 |
| WO | 2009/097470 A1 | 8/2009 |

OTHER PUBLICATIONS

International Search Report issued Oct. 30, 2013, in Application No. PCT/EP2013/070436, 4 pages.
Beutner, Stefan et al., "Synthetic Singlet Oxygen Quenchers," Methods in Enzymology, pp. 226-241, vol. 319.
Cuatrecasas, Pedro, "Protein Purification by Affinity Chromatography," The Journal of Biological Chemistry, Jun. 25, 1970, pp. 3059-3065, vol. 245, No. 12.

*Primary Examiner* — Jeremy C Flinders
(74) *Attorney, Agent, or Firm* — Roche Diagnostics Operations, Inc.

(57) ABSTRACT

The present invention relates to a method of specifically releasing a one or more members of a sub-group of objects from an entity, a method of detecting a subject's disease by detecting one or more members of a sub-group of biological entities indicative of the disease and a method of isolating one or more members of a sub-group of objects from a group of objects.

13 Claims, 3 Drawing Sheets

METHODS OF SPECIFICALLY RELEASING A SUB-GROUP OF OBJECTS

CROSS-REFERENCE TO RELATED APPLICATIONS

This application is a continuation of International Application No. PCT/EP2013/070436 filed Oct. 1, 2013, and claims priority to EP Patent Application No. 12006876.2 filed Oct. 2, 2012, the disclosures of which are hereby incorporated by reference in their entirety.

BACKGROUND OF THE INVENTION

The present invention relates to a method of specifically releasing a one or more members of a sub-group of objects from an entity, a method of detecting a subject's disease by detecting one or more members of a sub-group of biological entities indicative of the disease and a method of isolating one or more members of a sub-group of objects from a group of objects.

In modern research, the availability and selection of a suitable assay is a decisive step. Therefore, a multitude of different assay designs has been developed. In health care, assays may be used to detect particular chemical, biochemical or biological compounds or entities, i.e., proteins, nucleic acids, ligands or cells, which have been correlated or are associated with various disease conditions. In the field chemistry or pharmacy, screening assays for the identification of targets are particularly suitable, as they usually allow for the screening of multitude of compounds in one assay design and allow for rather quick identification of new, valuable chemical, biochemical or biological compounds or entities. Many of these tests are based on the selective binding to a target of interest. In general, assay designs can be sub-classified into between homogenous assays and heterogenous assays.

Homogenous assays are those not involving a separation step. Homogenous assays may be used if the target differs from other compounds and can be detected based on this difference. An example would be an assay including a labeling of a target entity. If the labeled target entity behaves differently than a non-labeled non-target entity, no separation step would be required.

One possibility of detecting targets in a homogenous assay is by proximity assays. Proximity assays are based on the binding of a "detecting agent" to a target. Upon the binding, a signal is generated due to the proximity of the target to the detecting agent. For example, in scintillation proximity assays or fluorescence resonance energy transfer (FRET) assays, energy is transferred from the target to the detecting agent. In other formats, a catalytic reaction may be allowed (e.g. by the proximity of an enzyme to its substrate).

Heterogenous assay require a separation step. In heterogenous assay formats, target entities are usually separated form non-target entities and detected thereafter. Therefore, heterogenous test require that at least one component of the test is attached to an entity or support, preferably a solid support. Accordingly, the term "heterogeneous assay" as used herein refers to an assay method, wherein at least one of the reactants in the assay mixture is attached to an entity or support allowing for separation, such as a solid support.

Homogeneous are most desired from an operational standpoints since the entire reaction and an addition of reagents for the performance of the assay, take place in a single solution along with the final detection step. Accordingly, mechanical manipulations, which are time-consuming and can cause errors, are avoided; however, the technical aspects of developing such an assay with the desired sensitivity are substantial. In contrast, numerous assays are performed on a heterogeneous basis in that certain steps are performed in one solution which includes some type of solid phase material. The reaction to be detected takes place on the solid phase and is then followed by a separation step, whereby unreacted components, and thus contaminating influences, may be effectively removed. The result is generally a higher level sensitivity at the expense of additional mechanical manipulations.

BRIEF SUMMARY OF THE INVENTION

The present invention relates to a method of specifically releasing a one or more members of a sub-group of objects from an entity, a method of detecting a subject's disease by detecting one or more members of a sub-group of biological entities indicative of the disease and a method of isolating one or more members of a sub-group of objects from a group of objects.

BRIEF DESCRIPTION OF THE FIGURES

FIG. 1A: shows a heterogeneous group of objects (large circles with surface structure variants ○, ∇, □ and ◆) comprising a homogeneous subgroup of objects (indicated in black color and comprising variant ◆). The group of objects is bound to a solid support (hatched area) via linkers (meandering lines connecting objects with solid support). The group of objects is contacted with an identifier (black object at the top of FIG. 1 A) capable of specifically binding the surface target present on the black subgroup of objects. The identifier is coupled to a releaser (illustrated by scissors) capable of releasing the subgroup from the solid support by interacting with the linker.

FIG. 1B: shows the releaser is brought in proximity to the linker upon binding of the identifier to the black subgroup.

FIG. 1C: the black subgroup of objects is specifically released from the solid support by cleavage of the linker.

DETAILED DESCRIPTION OF THE INVENTION

It was an object of the present invention to provide a new assay concept.

This object has been solved by combining the advantages of heterogeneous assays with those of proximity assays. Accordingly, in a first aspect, the present invention provides a method of specifically releasing one or more members of a sub-group of objects from an entity, preferably a solid support, the method comprising
  a) providing a heterogeneous group of objects comprising a homogeneous subgroup of objects, each member of the group of objects being bound to an entity, preferably a solid support via a linker;
  b) contacting the group of objects with an identifier, being capable of specifically binding the subgroup of objects, under conditions allowing the binding of the identifier to the subgroup of objects, wherein the identifier is coupled to a releaser being capable of releasing a member of the subgroup from the entity by interacting with the linker;
  c) binding the identifier to the subgroup, thereby bringing the releaser in proximity to the linker; and d) specifically releasing one or more members of the subgroup from the entity by allowing interaction between the releaser and the linker, thereby specifically releasing the one or more members of the subgroup of objects from the entity.

As detailed above, the present invention is based on combining heterologous assays with proximity assays. Accordingly, the present invention describes a new assay design; therefore, the nature of the components used in the method of the present invention is not decisive.

Figure 1A:
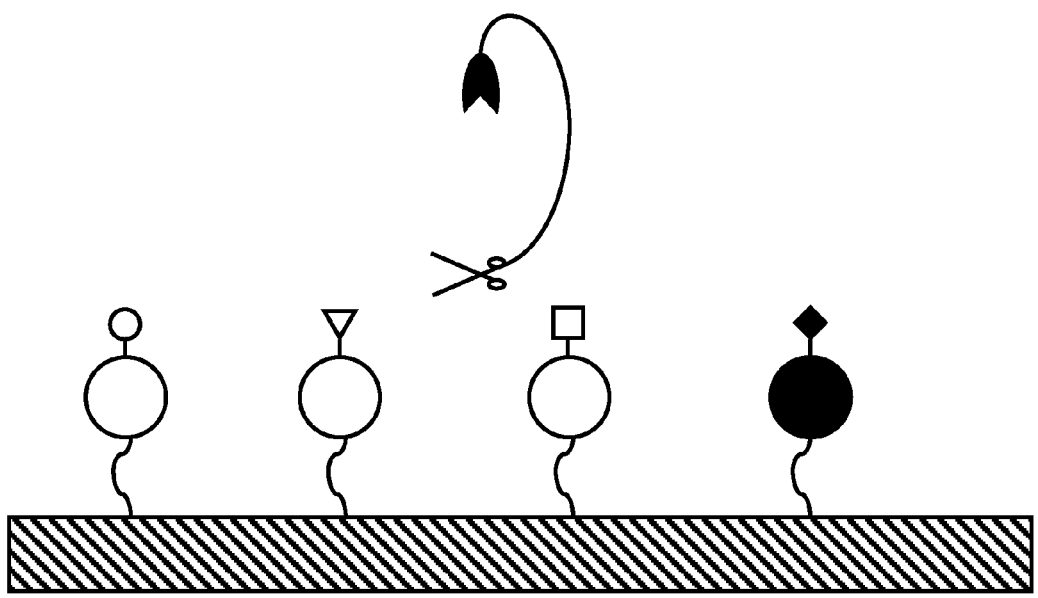
FIG. 1A-C illustrates a method for specifically releasing a sub-group of objects from a solid support.
Figure 1B:
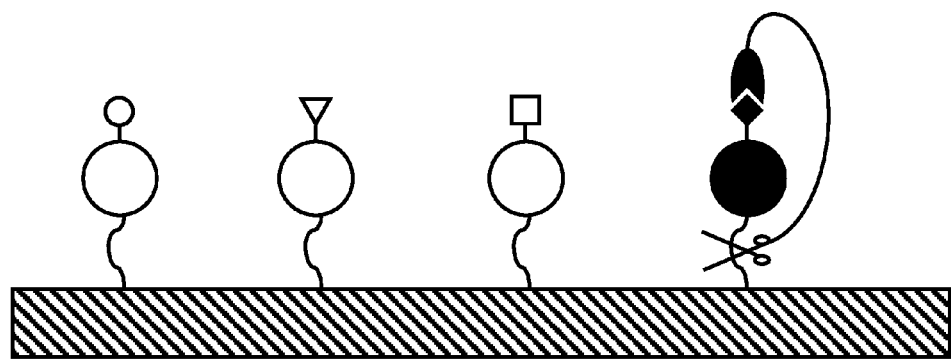
Figure 1C:
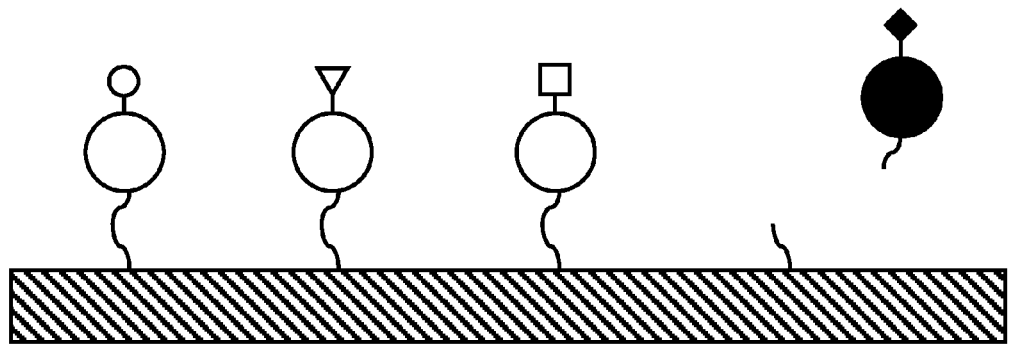

For illustration purposes, the design or concept of the method of the present invention is also shown in FIG. 1, wherein FIG. 1 is not intended to limit the scope of the claimed method. FIG. 1 A shows a heterogeneous group of objects (large circles with variants ○, ∇, □ and ♦) comprising a homogeneous subgroup of objects (indicated in black color and comprising variant ♦). The group of objects is bound to a support (hatched area) via linkers (meandering lines connecting objects with solid support). The group of objects is contacted with an identifier (black object at the top of FIG. 1 A) capable of specifically binding the surface target present on the black subgroup of objects. The identifier is coupled to a releaser (illustrated by scissors) capable of releasing the subgroup from the solid support by interacting with the linker. In FIG. 1B, the releaser is brought in proximity to the linker upon binding of the identifier to the black subgroup. In FIG. 1C, the black subgroup is specifically released from the support by cleavage of the linker.

The term "specifically releasing" with respect to the sub-group of objects is intended to mean that the member(s) of the sub-group of objects is preferentially released in comparison to the remaining members of the group of objects. As detailed above, the releasing is due to the interaction of the releaser and the linker. This interaction is allowed due to the identifier-mediated proximity of the releaser to the linker. However, the skilled person will understand that proximity of the releaser to any linker may also occur accidentally, which is not regarded as specifically releasing, as it is rather a background signal and not based on a specific binding of the identifier to the target object. In a preferred embodiment, the number of objects released by "unspecific releasing" (i.e. the releasing caused by unspecific effects, e.g. accidental proximity, or background releasing) is at most 20% of the number of objects released by "specific releasing", preferably at most 10%, more preferably at most 5%, still more preferably at most 4%, 3%, 2%, or 1%.

"Specific" or "specificity" in reference to the binding of one molecule to another molecule, such as the binding of the identifier to the target object, means the recognition, contact, and formation of a stable complex between the identifier and the target object, together with substantially less recognition, contact, or complex formation of the identifier with objects other than the target object (also referred to as other objects). In one aspect, "specific" in reference to the binding of the identifier to the target object means that to the extent the identifier recognizes and forms a complex with the target object, it forms the largest number of the complexes with the target object in comparison to the other objects. In one aspect, this largest number is at least 50% of all such complexes form by the identifier with the target object, preferably at least 75%, more preferably at most 80% or 90%, still more preferably at most 95%, 96%, 97%, 98% or 99%. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

The term "heterogeneous group of objects" means that not all members of the group of objects are identical. One or more members of the group differ form other members in at least one feature. These one or more members are referred to as homogenous sub-group of objects or target objects. For example, the heterogenous group of objects may be cells obtained from a patient's blood and may comprise different cell types, e.g. expressing different surface markers. The identifier could be directed against a particular surface protein characterizing a specific sub-type of cells, e.g. a cancer cell, which would allow for the specific release of cancer cells and could be used in the identification of cancer cell in a patient's sample. In another example, a library of compounds could be screened, e.g. in order to identify a binding partner for a target molecule. This target molecule could be a target in the treatment of a disease, e.g. an enzyme or a receptor. Examples of chemical compound libraries include without limitation beta-lactams; hydantoin imides and thioimides; imidazoles; N-acyl-alpha-amino amides, esters, acids; oxazoles; phosphonates (alpha-hydroxy, alpha-amino, alpha-acylamino); phosphinates; pyrroles; tetra-substituted 5 membered ring lactams; tetra-substituted 6 membered ring lactams and tetrazoles.

In contrast thereto, the "homogeneous subgroup of objects" characterizes a subgroup of objects encompassed in a group of objects, wherein the members of the subgroup are identical with respect to one feature. The presence of this feature (e.g. a structural domain or entity) is decisive for the binding of the identifier, i.e. all objects of this subgroup are bound by the identifier due to the presence of this feature. As detailed above, this feature may be a surface structure of a cell (e.g. a surface protein or receptor) or a domain of a chemical compound. The members of the subgroup may be identical (e.g. identical chemical compounds or cells) or may differ in features other than the one defining homogeneity (e.g. different types of cells expressing a particular surface receptor). In one embodiment of the invention the homogenous subgroup of objects may be a group of identical objects or even only one object. Alternatively, the subgroup of objects may be a group of diverse objects identical only with respect to one or more, but not all features.

In accordance with the present invention, the entity from which the subgroup is specifically released allows for separating of the one or more members of the homogeneous subgroup of objects from the remaining members of the heterogeneous group of objects. In a preferred embodiment the entity is a support, more preferably a solid support, as detailed below. Evidently, specific release from a solid support allows for this separation step.

In one embodiment, the group of subjects could be in a magnetic liquid, e.g. comprising nanoparticle in a stable suspension. The members of the group could be bound to the nanoparticles and specifically released upon the binding of the identifier. Accordingly, the entity could be nanoparticles, such as magnetic nanoparticles.

Alternatively, the entity could be other means allowing for specific separation such as a label. The label may be a tag or marker (see below) and is bound to the members of the group via a cleavable linker. Upon the binding of the identifier to the subgroup, the label is removed from the member of subgroup, whereas the other members of the group remain labeled. The label is recognized by a binding partner and the separation is based on the separation of labeled and unlabelled members. In one example, the label may be streptavidin and the separation takes place due to the capability of streptavidin-labelled members to bind to biotin, which might be e.g. coupled to a solid phase. In this example unlabelled target members remain in solution.

Alternatively, a sorting mechanism based on the presence and absence of the label could be used, which is exemplarily detailed below for fluorescence-activated cell sorting Fluorescence-activated cell sorting (FACS). However, the skilled person will understand that this principle is neither limited to cells nor to fluorescent labels. FACS is a specialized type of flow cytometry. It provides a method for sorting a heterogeneous mixture of biological cells into two or more containers, one cell at a time, based upon the specific light scattering and fluorescent characteristics of each cell. It is a useful scientific instrument, as it provides fast, objective and quantitative recording of fluorescent signals from individual cells as well as physical separation of cells of particular interest. Typically, the cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

A wide range of fluorophores can be used as labels in flow cytometry. Fluorophores are typically attached to an antibody that recognises a target feature on or in the cell; they may also be attached to a chemical entity with affinity for the cell membrane or another cellular structure. Each fluorophore has a characteristic peak excitation and emission wavelength, and the emission spectra often overlap. Consequently, the combination of labels which can be used depends on the wavelength of the lamp(s) or laser(s) used to excite the fluorochromes and on the detectors available. Quantum dots are sometimes used in place of traditional fluorophores because of their narrower emission peaks. In one approach to overcoming the fluorescent labeling limit, lanthanide isotopes are attached to antibodies. Cells are introduced into a plasma, ionizing them and allowing time-of-flight mass spectrometry to identify the associated isotopes.

For example, the label may be any label which can be specifically identified by a binding partner and which can be bound to the members of the group via a cleavable linker. Examples include tags, antibodies, antigens, commercial markers, proteins, receptors, nucleic acids, etc, as also derailed herein.

Preferably, the entity or support is a solid support. The term "solid-support" refers to a material in the solid-phase that interacts with reagents in the liquid phase by heterogeneous reactions. The use of solid supports is well known in the fields of chemistry, biochemistry, pharmacy and molecular biology. Many types of solid supports have been developed depending on the technical problem to be solved. Any of these may be used in the context of the present invention. For example, the solid support used in the methods of the present invention may include components of silica, cellulose acetate, nitrocellulose, nylon, polyester, polyethersulfone, polyolefin, or polyvinylidene fluoride, or combinations thereof. Further suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

Common resin supports used e.g. in combinatorial or protein chemistry include polystyrene resin, e.g. cross-linked with divinylbenzene; hydroxymethylpolystyrene; aminomethylpolystyrene; TentaGel resin (TG) and ArgoGel (AG): polystyrene/DVB-poly(ethylene glycol) graft copolymers (PS-PEG)—Bayer; Crowns/Pins (CP) (radiation-grafted polyethylene/polypropylene support); Kieselguhr/polyacrylamide-based resins (KPA); Controlled-pore glass; PEGA—poly(ethylene glycol)/dimethylacrylamide copolymer.

Immobilization or binding to the entity or solid support may be accomplished using solid supports that have been modified or activated to include functional groups that permit the covalent coupling of the entity or support to the object, e.g. a protein. Typically, aliphatic linker arms are employed. The objects, particularly proteins, can also be noncovalently attached to a surface, through, for example, ionic or hydrophobic mechanisms, and are detached by the releaser inhibiting these mechanisms locally. Additionally, covalent attachment of an object, e.g. a protein or nucleic acid, to a surface, e.g. a glass or metal oxide surface, can be accomplished by first activating the surface with an amino silane. Objects derivatized with amine-reactive functional groups can then attach to the surface. Entities or (solid) supports can be derivatized with proteins such as enzymes, peptides, oligonucleotides and polynucleotides by covalent or non-covalent bonding through one or more attachment sites, thereby binding the same acid to the entity or the solid support.

The entity/(solid) support may be contained in a vessel, wherein the vessel is a tube, such as a centrifuge tube or spin tube, syringes, cartridge, chamber, multiple-well plate, or test tube, or combinations thereof. The entity/(solid) support may be pre-treated or functionalized in order to allow linker-mediated binding of the objects. In one embodiment, the solid support may be fibrous or particulate usually allowing for appropriate contacting. The size of the entity/(solid) support suitable for use with the reagents of this invention may vary according to method chosen.

The objects of heterogeneous group may be bound to one entity/(solid) support only (e.g. one vessel or multi-well plate) or may be bound to a multitude of entities/(solid) supports (e.g. beads). The shape of the entity/(solid) support suitable for use in the methods of this invention may be, for example, a sheet, a precut disk, cylinder, single fiber, or a solid support composed of particulates. In one embodiment, the entity/(solid) support may be fibrous or particulate to allow optimal contacting. The size of the entity/(solid) support may vary and may be chosen depending from the method to be carried out.

Since the introduction of the Merrifield resin, libraries of peptides, nucleotides, and organic molecules have been generated on solid supports. As detailed above, entities/ supports may be functionalized, e.g., by including polar functionalities such as carboxylic acids, amides, alcohols and thiols, as many of the linkers available for solid support synthesis to date require polar functional groups for binding. In some embodiments polar functionalities may possess unfavorable pharmacological properties. Because of poor oral bioavailability and enzymatic degradation of linear peptides, modified peptides, peptidomimetics, and cyclic peptides have become appealing targets for the design of therapeutic agents with increased pharmacological activities. For non-polar or aromatic compounds other supports may be more desirable, such as those having a hydrophobic aliphatic or aromatic carbon chain. Additionally, resin-bound arylsilane have been developed for the solid phase synthesis of aromatic or heteroaromatic compounds.

However, suitable solid supports also include silica-based supports such as glass fiber, glass beads, glass particles, glass powder, silica particles, and glass micro fibers. The glass may be borosilicate glass. Glass according to the present invention is understood to be an amorphous material that contains silicium. Glass can contain other materials such as B2O3 (0-30%), Al2O3 (0-20%), CaO (0-20%), BaO (0-10%), K2O (0-20%), Na2O (0-20%), MgO (0-18%) and Pb2O3 (0-15%). Glass can also contain a smaller percentage (0-5%) of a number of other oxides such as $Mn_2O_3$, $TiO_2$, $As_2O_3$, $Fe_2O_3$, CuO, CoO, etc.

The entity/support may be encased or immobilized in a vessel to enable plug-flow or continuous-flow methods. Alternatively, the material of the entity/support may be packed so as to create a free-standing entity/(solid) support such as a membrane, disk, or cylinder that may be immobilized or encased in a suitable vessel, such as a tube or plate. If necessary, the entity/support is contained in an appropriate vessel, e.g., a paper form (such as a Guthrie card), a microcentrifuge tube, a spin tube, a 96-well plate, a chamber, or a cartridge.

Conventional heterogeneous assays employ dipsticks which may be easily removed from the solution by hand, or large beads which similarly allow facile transfer. Smaller beads, generally of latex or similar materials, have been employed and have relied upon filter and/or centrifugal methods for their sequestration from the fluids. The concept of employing large magnetic particles has also been explored. Specifically, particles and their removal from solution by the employment of electromagnetic energy are known in the art.

In a preferred embodiment, the solid support is a multiple well plates, for example, 6, 12, 24, 48, 96, or 384 well plates or is a solid support packed into each well.

In accordance with the present invention, the objects are bound to the entity/support via a linker. The linker may be any suitable domain (i) capable of binding the objects to the entity/support and (ii) being capable of releasing the subgroup from the entity/support due to interaction with the releaser. The selection of a suitable linker will depend on the (i) type of objects, (ii) the entity/support and (iii) the releaser/releasing mechanism. The ordinarily skilled artisan will know numerous other schemes for linking chemical compounds, nucleic acids, proteins, cells or other objects to support surfaces. Moreover, the choice of the entity/support surface and the method of immobilizing are largely a matter of convenience and depend on the practitioner's familiarity with, and preference for, various supports surfaces, as well as preference for various immobilizing schemes, and knowledge of the releaser. The linker may be bound to the entity/support by being covalently or non-covalently attached to the surface of the entity/support or incorporated into the body of the entity/support. Linking to the surface may be accomplished as discussed herein. The linker may be incorporated into the body of the support either during or after the preparation of the support. The linkers used in order to bin d the objects to the entities/supports may be structurally identical or different. However, structurally identical linkers are preferred.

The linkers may be classified according to the cleavage reaction, e.g.
   Electrophilically cleaved linkers (e.g. cleavage acids such as Wang, Sasrin, and Rink linkers)
   Nucleophilically cleaved linkers (e.g. cleavage by bases)
   Photocleavable linkers
   Metal-assisted cleaved linkers
   Linkers cleavable under reductive conditions
   Linkers cleavable under oxidative conditions
   Linkers cleavable by cycloaddition and cycloreversion
   Electrochemically cleaved linkers
   Enzymatically cleavable linkers
   Non-covalently linkers (release by inhibiting binding mechanism locally)

Accordingly, a larger variety of linkers can be used, since cleavage may employ various types of chemical, photochemical, or enzymatic cleavage of a variety of cleavable linking groups, such as are known in the art. For example, non-limiting examples of chemically cleavable linkages include disulfides (cleavable by reduction, typically using dithiothreitol), azo groups (cleavable with dithionate), sulfones (cleavable with basic phosphate, with or without dithiothreitol), glycols, cleavable by periodate, and esters, cleavable by hydrolysis. Photolabile linkers include, for example, azo linkages and o-nitrobenzyl ethers.

The linker may be oxidation labile, preferably a thioether or its selenium analog; or an olefin, which contains carbon-carbon double bonds, wherein cleavage of a double bond to an oxo group, releases the target object. Illustrative thioether bonds are disclosed in Willner et al, U.S. Pat. No. 5,622,929. Illustrative olefins include vinyl sulfides, vinyl ethers, enamines, imines substituted at the carbon atoms with an [alpha]-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. References for such reactions and linkers are described in US 2005/0079565 A1.

Illustrative cleavable linkages include 3-thiolacrylic acid, N-methyl 4-amino-4-butenoic acid, 3-hydroxyacrolein, N-(4-carboxyphenyl)-imidazole, oxazole, and thiazole. Also of interest are N-alkyl acridinyl derivatives as described in US 2005/0079565 A1.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the target object.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the molecular tag. The rings may be coumarin, benzoxazine, tetralin, etc.

In the methods of the present invention, an identifier is used in order to identify the one or more members of the homogeneous sub-group of objects. As detailed above, the homogenous sub-group of objects is characterized by a common structural domain not present at or in the remaining members of the group of objects. The identifier recognizes this common structural domain and binds thereto. In order to allow for good accessibility, this structure is preferably located on the surface of the members of the homogeneous sub-group of objects. Accordingly, the identifier may be any entity (i) specifically recognizing the common structural domain of the homogeneous sub-group of objects (i.e. a surface target present on the members of the subgroup) and (ii) being capable of binding thereto.

In the biology, the key-lock principle is a basic principle realized in many processes. The idea is that a substance needs to fit in a certain way into a partner in order to allow for a specific reaction. Accordingly, a variety of substances and corresponding partner are known including enzyme and substrates, receptors and naturally occurring (e.g. transmitters, modulators or hormones) or artificial ligands (e.g. drugs), antigen and antibody and nucleic acids and its reverse transcripts. Also cells in tissues have surface structures and compliments allowing for communication as well as structural and functional unity. Further examples of cells requiring surface structural include immune cells in order to recognize targets and homings, sperms in order to enter in to an ovum and virus in order to infect a host.

Furthermore, many diagnostic methods are based on the key-lock principle such as blood typing, tissue typing, detecting of infections, and detection of specific DNA. However, specific recognition of targets and binding thereto is not limited to biology, but also an essential principle in chemistry.

Accordingly, the identifier and partner (also referred to as compliment or binding partner) may be any chemical, biochemical or biological compounds or entities fulfilling the above functional requirements, i.e. the identifier is capable of (i) specifically recognizing the partner and (ii) binding thereto. Examples of identifier/partner interactions include antibody-antigen interactions, enzyme-substrate interactions, formation of duplexes or triplexes among polynucleotides and/or oligonucleotides, receptor-ligand interactions, and the like.

In the methods of the present invention, a releaser is coupled to an identifier and is used to release the subgroup from the entity/support by interacting with the linker. The releaser has a cleavage-inducing moiety that may cleave the linker, e.g. at a susceptible bond, within its immediate proximity.

The releaser has to be selected based on the nature of the linker and the intended methods of cleaving the linker (see above). The releaser may be capable of producing a local acidic or basic environment in order to mediate electrophil or nucleophil cleavage, respectively. Releasers emitting light or singlet oxygen may be employed for photo- or photochemical cleavage. The releaser may be capable of producing a local reductive or oxidative environment in order to mediate cleavage under reductive or oxidative conditions, respectively. The releaser may comprise and enzyme or enzyme domain in order to allow for enzymatic cleavage of the linker. However, it is important that the action of the releaser is limited to the local environment in order to maintain specificity of the releasing.

Examples of releasers may be:
Enzmyes, such as nucleases and proteases
Photosensitizers
Sensitizers In one embodiment the releaser may be an enzyme, such as a restriction enzyme (or restriction endonuclease) which is an enzyme that cuts double-stranded or single stranded DNA at specific recognition nucleotide sequences known as restriction sites. Such enzymes, found in bacteria and archaea, are thought to have evolved to provide a defense mechanism against invading viruses. Inside a bacterial host, the restriction enzymes selectively cut up foreign DNA in a process called restriction; host DNA is methylated by a modification enzyme (a methylase) to protect it from the restriction enzyme's activity. Collectively, these two processes form the restriction modification system. To cut the DNA, a restriction enzyme makes usually two incisions, once through each sugar-phosphate backbone (i.e. each strand) of the DNA double helix. Restriction enzymes recognize a specific sequence of nucleotides and produce a double-stranded cut in the DNA. While recognition sequences vary usually between 4 and 8 nucleotides, many of them are palindromic. Exemplary restriction enzymes used frequently in biotechnology include EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SpeI, SphI, StuI and XbaI. Evidently, restriction enzymes are of particular use for nucleic acid linkers and the cleavage sites of the above enzymes are well known to the skilled person.

Alternatively, the enzyme may be a protease for cleaving peptide or protein linkers. Exemplary proteases include Arg-C proteinase, Asp-N endopeptidase, Caspase1, Caspase2, Caspase3, Caspase4, Caspase5, Caspase6, Caspase7, Caspase8, Caspase9, Caspase10, Chymotrypsin, Clostridiopeptidase B, Enterokinase, Factor Xa, Glutamyl endopeptidase, GranzymeB, Igase, Kex2, LysC, LysN, Pepsin, PreScission (human Rhinovirus 3C protease), Prolineendopeptidase, Proteinase K, Staphylococcal peptidase I, Tobacco etch virus protease, Thermolysin, Thrombin and Trypsin. Again, cleavage sites are well known to the skilled person.

However, also non-enzyme compounds may be used for the cleavage peptides including BNPS-skatole, CNBr, formic acid, hydroxylamine, iodosobenzoic acid and NTCB (2-nitro-5-thiocyanobenzoic acid). BNPS-skatole [2-(2-nitrophenylsulfenyl)-3-methylindole] is a mild oxidant and brominating reagent that leads to polypeptide cleavage on the C-terminal side of tryptophan residues.

Further enzymes which may be used for cleavage of carbohydrate linkers include amylases, xylanases, cellulases and ligninases.

The releaser may be a group that produces an active species that is capable of cleaving a cleavable linkage, e.g. by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226-241 (2000).

Releasers acting by a active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH.

The active species generated by the releaser may by a reactive intermediate, or species, usually singlet oxygen. Such a releaser may be a photosensitizer. Photosensitizers are sensitizers for generation of singlet oxygen by excitation with light. The photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm. The lifetime of an excited state produced following absorption of light in the absence of oxygen will usually be at least about 100 nanoseconds, preferably, at least about 1 millisecond. In general, the lifetime must be sufficiently long to permit cleavage of the linker.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures.

Examples of photosensitizers and methods involving the same are described in US 2005/00795656 A1 and references cited therein.

Other sensitizers included within the scope of the invention are compounds that on excitation by heat, light, ionizing radiation, or chemical activation will release a molecule of singlet oxygen. The best known members of this class of compounds include the endoperoxides such as 1,4-bis-carboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed US 2005/00795656 A1.

Coupling of the identifier to the releaser may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970). A wide variety of functional groups is available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a binding agent may vary widely, depending upon the nature of the compound being linked, the effect of the distance on the specific binding properties and the like.

In accordance with the present invention, the releaser is brought in proximity to the linker upon the binding of the identifier to a member of the sub-group. The releaser has a cleavage-inducing moiety that may be induced to cleave the linker, e.g. at a susceptible bond, within its immediate proximity. In accordance with the method, the cleavable linkages are brought within the effective cleaving proximity of the cleavage-inducing moiety so that the target object can be released. Evidently, the effective proximity will depend from the nature of the releaser and the nature of the cleavable linkage of the linker.

The releaser releases one or more members of the sub-group of objects, i.e. the target objects, from the entity/support by interacting with the linker. The interaction may be a direct interaction, wherein the releaser itself acts on the linker, thereby cleaving the linker and releasing the target object. An example of such a releaser is an enzyme catalyzing the cleavage of the linker such as a nuclease releaser cleaving a nucleic acid linker or a protease cleaving a peptide or protein linker. Alternatively, the interaction may be an indirect interaction, wherein the releaser mediates the production of a compound or environment cleaving the linker and releasing the target object. Examples of such releasers include those causing an acidic or basic milieu for the cleavage of electrophilically cleaved or nucleophilically cleaved linkers or a photosensitizer producing singlet oxygen acting on singlet oxygen-sensitive linkers, thereby releasing the target object. Furthermore, the release may be triggered, i.e. it may depend from the presence of a further factor (e.g. a chemical cofactor, light, temperature, pH, ions) which may be applied at an intended time.

Guidance for selecting releasers, cleavable linkages, and other components are disclosed in the following references: International patent publications WO 00/66607; WO 01/83502; WO 02/95356; WO 03/06947; U.S. Pat. No. 6,322,980 and U.S. Pat. No. 6,514,700.

As a first step of the method of the present invention, a heterogeneous group of objects comprising a homogeneous subgroup of objects is provided, wherein each member of the group of objects is bound to an entity or support, preferably a solid support, via a linker.

As a next step of the method of the present invention, the group of objects is contacted with an identifier. The group of objects may be added to the releaser or the releaser may be added to the group of objects. Usually, the contacting is an aqueous solution. The contacting is for a time and under conditions suitable for allowing the binding of the identifier to the subgroup of objects. The contacting may be in one vessel or in separate vessels and it may be possible to contact the group in several portions, e.g. one member of the group per vessel.

Suitable conditions include appropriate temperature and solution to avoid e.g. undesired chemical modifications of compound, loss of binding capability, denaturation of proteins involved or to maintain viable cells, if present. Suitable conditions will depend from the particular assay design and components chosen and the skilled person will be able to select the same based on his general knowledge. Incubation steps can vary from about 5 seconds to several hours, preferably from about 5 minutes to about 24 hours. However, the incubation time will depend upon the assay format, marker, volume of solution, concentrations and the like. Usually, the assays will be carried out at ambient temperature, although they can be conducted over a range of temperatures, such as 10° C. to 100° C. or 15° C. to 40° C.

As detailed above, the releaser is brought in proximity to the linker, if the identifier is bound to the subgroup. Then, one or more members of the subgroup is/are specifically released from the entity/support by the interaction between the releaser and the linker.

The method may be used in combinatorial chemistry, drug screening, in the diagnosis or detecting of diseases. It may be combined with recent advances in robotic systems, which enable the testing of a large number of samples in a short period of time, is becoming an important tool in accelerating the above applications. Such screening technique involves the preparation of a large number of structurally related compounds or entities either as mixtures in the same reaction vessel or individually by parallel synthesis. In this manner large pools of similar compounds or entities can be prepared and analysed within a short period of time.

Chemical compound libraries include a plurality of chemical compounds and have been assembled from any of multiple sources, including chemical synthesized molecules or natural products, or have been generated by combinatorial chemistry techniques. They are especially suitable for high-throughput screening and may be comprised of chemical compounds of a particular structure or compounds of a particular organism such as a plant. In the context of the present invention, the chemical compound library is preferably a library comprising proteins and polypeptides or small organic molecules. Preferably a small organic molecule is less than 500 daltons in size, particularly a soluble, non-oligomeric, organic compound.

The libraries may be used, e.g. to identify nucleic acid aptamers, to identify ligands to cellular targets, such as receptor, to identify antibodies binding a target or an antigen binding a target antibody, compounds binding to target enzymes, to identify aminimide as mimetics, to identify enzyme inhibitors, to identify inhibitors of signal transduction or to identify inhibitors of receptors.

In one embodiment of the present invention, the method is carried out repeatedly, e.g. for sequential analysis of cells. In a first step, a first population of cells is released by the method of the present invention based on a surface structure identified by a first identifier. The cells are preferably separated from the remaining population of still bound cells. In a first alternative, the remaining population of cells may be contacted with a second identifier to release a second subpopulation of cells, and so on. In a second alternative, the released population of cells may be again bound to an entity and contacted with a second identifier and so on. Cells finally released are characterized by the presence of several surface structures, i.e. those recognized by the first, the second etc. identifier.

In a preferred embodiment of the present invention, the entity is a support, particularly a solid support. Further details are also given above.

In another preferred embodiment of the present invention, the objects are chemical, biochemical or biological compounds or units.

As detailed above, the method can be used in a variety of assay designs and the character of the object may vary depending on the intended use.

The method may be used in screening application, e.g. for screening for a chemical, biochemical or biological compound, unit or entity. Accordingly, the object may be any of these.

A chemical compound is a pure chemical substance consisting of two or more different chemical elements. Chemical compounds have a unique and defined chemical structure; they consist of a fixed ratio of atoms that are held together in a defined spatial arrangement by chemical bonds. Chemical compounds can be molecular compounds held together by covalent bonds, salts held together by ionic bonds, intermetallic compounds held together by metallic bonds, or complexes held together by coordinate covalent bonds.

Biochemistry is the study of chemical compounds and reactions which occur in living organisms. Accordingly, a biochemical or biological compound is a chemical compound naturally occurring in a living organism. This includes e.g. carbohydrates, lipids, proteins and nucleic acids, which are the types of molecules involved in the chemistry of living organisms.

However, the methods may not be limited to compounds, but may also relate to more complex or larger chemical, biochemical or biological entities. In the field of biology or biochemistry, this particularly includes cells or tissues or parts thereof, such as cell membranes, protein complexes, specific cells, tissue sections, organelles etc. In the field of chemistry, this particularly includes complexes of compounds, polymers, compositions, etc.

In another preferred embodiment of the present invention, the objects comprise or are proteins, nucleic acids, antigens, antibodies or functionally active derivatives thereof, accordingly, the objects may be composed of the above components only or may comprise further components or combinations of the above components.

Proteins are biochemical compounds consisting of one or more polypeptides. A polypeptide is a single linear polymer chain of amino acids bonded together by peptide bonds between the carboxyl and amino groups of adjacent amino acid residues. Generally, polypeptides are composed of 20 standard amino acids; however, the protein according to the present invention may also comprise further amino acids (e.g. selenocysteine or pyrrolysine) or modified amino acids (e.g. those listed in Table 4 of Annex 2 of WIPO-Standard ST.25, e.g. as published in Special edition No. 3/2007 OJ EPO). Furthermore, the residues in a protein may be chemically modified by post-translational modification. Additionally, a non-peptide group may be attached, e.g. a prosthetic group or a cofactor. In the context of the present invention, the protein is not define by a minimal size and may also comprise peptides.

The term nucleic acid is the over all name for polynucleotides and includes DNA and RNA. The basic component of biological nucleic acids is the nucleotide, each of which contains a pentose sugar (e.g. ribose or deoxyribose or di-deoxyribose), a phosphate group, and a nucleobase.

Nucleic acids may be generated within the laboratory, through the use of enzymes (DNA and RNA polymerases) and by solid-phase chemical synthesis. The chemical methods also enable the generation of altered nucleic acids that are not found in nature, for example peptide nucleic acids. Typical natural and modified nucleic acids are listed in Tables 1 and 2 of Annex 2 of WIPO-Standard ST.25, e.g. as published in Special edition No. 3/2007 OJ EPO.

An antigen is a substance/molecule that, when introduced into the body, triggers the production of an antibody by the immune system, generally intended to kill or neutralize the antigen that is recognized as a foreign and potentially harmful invader. The term originally came from antibody generator and was a molecule that binds specifically to an antibody, but the term now also refers to any molecule or molecular fragment that can be bound by a major histocompatibility complex (MHC) and presented to a T-cell receptor.

At the molecular level, an antigen is characterized by its ability to be "bound" at the antigen-binding site of an antibody. Antigens are usually proteins or polysaccharides.

This includes parts (coats, capsules, cell walls, flagella, fimbrae, and toxins) of bacteria, viruses, and other microorganisms. Usually, lipids and nucleic acids are only antigenic when combined with proteins and polysaccharides. Antigens are of particular relevance in the development of vaccines.

Naturally occurring antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

In addition to naturally occurring antibodies, artificial antibody formats (referred to a functionally active derivative in the context of the present invention) including antibody fragments have been developed. Some of them are described in the following. However, any other antibody format capable of binding to an antigen may be used.

Hence, "antibody" is intended to relate to an immunoglobulin-derived structure with specific binding, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition. The antibody may be any polypeptide which comprises at least one antigen binding fragment. Antigen binding fragments consist of at least the variable domain of the heavy chain and the variable domain of the light chain, arranged in a manner that both domains together are able to bind to the specific antigen.

An "antibody derivative" also contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv). Dissociation of scFvs results in monomeric scFvs, which can be complexed into dimers (diabodies or $(scFv)_2$), trimers (triabodies) or larger aggregates such as TandAbs and Flexibodies.

Antibodies with two binding domains can be created either through the binding of two scFv with a simple polypeptide link $(scFv)_2$ or through the dimerisation of two monomers (diabodies).

Certain antibody molecules including, but not limited to, Fv, scFv, diabody molecules or domain antibodies (Domantis) may be stabilized by incorporating disulfide bridges to line the VH and VL domains. Bispecific antibodies may be produced using conventional technologies, specific methods of which include production chemically, or from hybrid hybridomas) and other technologies including, but not limited to, the BiTE™ technology (molecules possessing antigen binding regions of different specificity with a peptide linker) and knobs-into-holes engineering.

Accordingly, exemplary functionally active derivatives of antibodies include a Fab, a Fab', a F(ab')2, a Fv, a disulfide-linked Fv, a scFv, a $(scFv)_2$, a bispecific antibody, a multi-specific antibody, a diabody, a triabody, a tetrabody or a minibody.

Exemplary target biochemical entities, in particular proteins, nucleic acids, antigens, antibodies or functionally active derivatives thereof, which may be released and optionally detected (presence or level) by the methods of the present invention, particularly in blood tests for a particular disease or condition include GHRH or IGF-1 (acromegaly), lipase (acute pancreatitis), anthrax (anthrax), smooth muscle cells (SMA) antibodies, antinuclear antibodies (ANA) (autoimmune hepatitis), prostate specific antigen (PSA) (benign prostate hyperplasia), anti-endomysium antibody, antireticulin antibody test, gluten antibodies, antigliadin antibody (celiac disease), aminotransferase (chronic hepatitis C), CMV antibody (cytomegalovirus), dengue antibodies (dengue fever), fructosamine, TSH, Vitamin B12, HbA1c (diabetes), airborne allergens (eczema), prolactin (female infertility), gastrin (gastrinoma), ferritin (hemochromatosis), aminotransferase, ALT, anti-HCV antibodies (hepatitis C), alpha-fetoprotein (AFP) (hepatoma), HIV antibody (HIV), testosterone (impotence), creatinine, urea nitrogen (BUN) (kidney conditions), gonadotropin (Klinefelter syndrome), antinuclear antibody (ANA), anticardiolipin antibody, anti-La (SSB) antibody, anti-Sm antibody test, anti-Ro (SSA) antibody, anti-DNA antibody, anti-RNP antibody (lupus), Lyme antibody (lyme disease), malaria antibody (malaria), LH, FSH (McCune-Albright syndrome), FSH (menopause), M protein antibody (multiple myeloma), acetylcholine receptor antibody (Myasthenia Gravis), CA-125 (ovarian cancer), prostatic acid phosphatase (PAP), prostate-specific antigen (PSA) (prostate cancer), ANA antibody, rheumatoid factor (rheumatoid arthritis), ACE (sarcoidosis), IgA, IgM, IgG (SCID), antinuclear antibodies (ANAs), SS-B antibodies (Sjogren's syndrome), Strongyloides antibody (strongyloidiasis), syphilis antibody (syphilis), TSH, thyroglobulin (thyroid cancer) and antineutrophil cytoplasmic antibodies (ANCA) (Wegener's granulomatosis).

In an even more preferred embodiment of the present invention, the heterogeneous group of objects comprising a homogeneous subgroup of objects is a heterogeneous population of cells comprising a homogeneous sub-population of cells.

As detailed above, the present invention is particularly suitable in the identification and detection of a subgroup of cells, e.g., in the detection of cancer cells from a population of cells. Accordingly, a group of cells may be attached to an entity/(solid) support and target cells may be identified using an appropriate identifier. The identifier is directed against a structure of the target cell, e.g. a surface structure such as a receptor or membrane protein. Upon the binding of the identifier, the target cell is released from the entity/(solid) support. Released cells may be isolated and further analyzed. Examples of target cells include: cancer cells such as circulating tumor cells or circulating tumor microemboli, particular blood cells, such as B cells, T cells, eosinophils, etc.

Still more preferably, the sub-population of cells consists of rare cells, particularly wherein in the population the ratio of rare cells to total cells is at most 5%, preferably at most 1%, especially at most 0.1%, such as at most 0.01%. The method is particularly useful in the identification of rare cells, as the method includes a separation by specifically releasing target cells only. Rare cells may be in particular circulating tumor cells (CTC) and circulating tumor micro-emboli (CTM) in a patient's blood. The technical challenge in this field consists of finding 'rare' tumor cells (just a few CTCs mixed with the approximately 10 million leukocytes and 5 billion erythrocytes in 1 ml of blood) and being able to distinguish them from other cells, particularly epithelial non-tumor cells and leukocytes. However, these cells may be detected long before the tumor itself is detectable by standard means (and therefore a first diagnostic tool), which is evidently highly advantageous in the treatment of the cancerous diseases.

Alternatively, in the population the ratio of cells of the homogeneous sub-population of cells to total cells is at most 50%, especially in the range from 5% to 50%, particularly in the range from 10% to 30%. This method may be used in order to detect a larger subpopulation of cell, e.g. cells of a particular type, such as particular blood cells. In this context, the method of the present invention may be used for cell sorting as usually done by FACS.

This embodiment is of particular interest for the isolation or detection of cells indicative of a particular state, such as a disease. It is particularly preferred if the sub-population of cells is indicative of a disease, particularly of cancer. Cancer cells are characterized by particular markers. Examples which may be mentioned are: especially oncogenes and tumor suppressor genes such as p53, genes of the ras family erb-B2, c-myc, mdm2, c-fos, DPC4, FAP, nm23, RET, WT1, and the like, LOHs, for example with regard to p53, DCC, APC, Rb and the like and also BRCA1 and BRCA2 in hereditary tumors, microsatellite instability of MSH2, MLH1, WT1 and the like; also tumorous RNAs such as CEA, cytokeratins, e. g. CK20, BCL-2, MUC1, in particular tumor-specific splice variants hereof, MAGE3, Muc18, tyrosinase, PSA, PSM, BA46, Mage-1 and the like, or else morphogenic RNAs such as maspin, hCG, GIP, motilin, hTG, SCCA-1, AR, ER, PR, various hormones and the like;—furthermore, especially RNAs and proteins which affect the metastasizing profile, i. e. the expression of molecules involved in angiogenesis, motility, adhesion and matrix degradation such as bFGF, bFGF-R, VEGF, VEGF-Rs, such as VEGF-R1 or VEGF-R2, E-cadherin, integrins, selectins, MMPs, TIMPs, SF, SF-R and the like, the cell cycle profile or proliferation profile, such as cyclins (e. g. expression ratio of cyclins D, E and B), Ki67, p120, p21, PCNA and the like, or the apoptosis profile, such as FAS (L+R), TNF (L+R), perforin, granzyme B, BAX, bcl-2, caspase 3 and the like.

Alternatively, the sub-population of cells is composed of cells of one cell type. The cells may be e.g. cardiovascular cells or vascular cells or vascular cells released by an inflammatory process or a fetal cell, e.g. a fetal cell in maternal blood, stem cells (e.g. cancerous stem cells), cells indicative of a minimal residual disease, cancer cells (e.g. leukemia cells). In this context, the method may be used for genotyping, diagnosis, prognosis, monitoring treatment etc.

The identifier may be characterized in that it comprises or is a biological, biochemical or chemical entity or unit; particularly a protein or a nucleic acid, especially an antibody or functionally active derivative thereof, a receptor or a binding site thereof, an enzyme or a binding site thereof, a tag-binding site, a ligand to a receptor, a substrate to an enzyme or a tag. In addition to the definition of tag given herein, the tag may be a small molecule capable of binding as an artificial ligand.

The biological, biochemical or chemical entity/unit, the protein, the nucleic acid and the antibody or functionally active derivative thereof may be defined as described above in the context of the objects used in the methods of the present invention.

In preferred embodiments, the identifier may be selected in order to screen for a binding partner to a target molecule or entity within a group of objects (e.g. a potential pharmaceutical for a target receptor) or it may be selected in order to identify a target object within a group of objects (e.g. a marker for a disease in a blood sample). Accordingly, suitable identifiers may include a receptor or a binding site thereof, an enzyme or a binding site thereof, a tag-binding site, a ligand to a receptor, a substrate to an enzyme or a tag. As detailed above, pairs of entities such as receptors and their ligands; enzymes and their substrates or analogs thereof; tags and their binding sites as well as antigens and antibodies directed against them act via key-lock principle. Accordingly, one component of the pair may be used as identifier for the other (i.e. the target).

G protein-coupled receptors are found only in eukaryotes, including yeast, plants, choanoflagellates, and animals. G protein-coupled receptors (GPCRs) constitute a large protein family of transmembrane receptors that have the ability to sense molecules outside the cell and activate inside through signal transduction pathways and ultimately induce cellular responses. The ligands that bind and activate these receptors range from light-sensitive compounds, odors, pheromones, to hormones and neurotransmitters, varying in size from small molecules to peptides and large proteins. G protein-coupled receptors are involved in many diseases, and serve as targets for almost half of all modern medicinal drugs.

Exemplary pairs of receptors/ligands or binding sites include:

Muscarinic acetylcholine receptor (Acetylcholine, Muscarine, Carbachol)
Adrenoceptors (Adrenaline, bupranolol)
GABA receptors, (γ-Aminobutyric acid or GABA)
Angiotensin receptors (Angiotensin)
Dopamine receptors (Dopamine)
Metabotropic glutamate receptors (Glutamate)
Histamine receptors (Histamine)
Serotonin receptors, (Serotonin)
Somatostatin receptors (Somatostatin)
Chemokine receptors (Chemokines)

As detailed above, enzymes may be used in this context. Examples of enzymes are given above.

Also protein A, protein G, protein A/G and protein L are known for their capability to spefically bind to proiteins, These proteins are immunoglobulin-binding bacterial proteins which are all commonly used to purify, immobilize or detect immunoglobulins. Each of these immunoglobulin-binding proteins has a different antibody binding profile in terms of the portion of the antibody that is recognized and the species and type of antibodies it will bind.

A number of (affinity) tags or (affinity) markers are known at present. These are usually divided into 3 classes according to their size: small tags have a maximum of 12 amino acids, medium-sized ones have a maximum of 60 and large ones have more than 60. The small tags include the Arg-tag, the His-tag, the Strep-tag, the Flag-tag, the T7-tag, the V5-peptide-tag and the c-Myc-tag, the medium-sized ones include the S-tag, the HAT-tag, the calmodulin-binding peptide, the chitin-binding peptide and some cellulose-binding domains. The latter can contain up to 189 amino acids and are then regarded, like the GST- and MBP-tag, as large affinity tags.

Exemplary pairs of tags/tag-binding sites include:
6×His/Hexa·His antibody
5×His/Penta·His antibody
RGSHHHH/RGS·His Antibody
4×His/Tetra·His Antibody
GST-tag/GST-tag antibody
Strep tag/Streptavidin
Biotin/Streptavidin
GST-tag/GST antibody
A Flag-tag (e.g. DYKDHD or DYKDDD)/Flag-tag antibody Furthermore, a hapten and the respective antibody may be used. A hapten is a small molecule with high immunogenicity used in many molecular biology applications. Popular haptens include digoxigeninDNP (dinitrophenol), biotin, and fluorescein.

Moreover, lectins such as concanavalin A, may be used as identifier, which can bind specific carbohydrate molecules. The most common application is to identify proteins based on their glycosylation groups.

Likewise, aptamers may be used as identifiers. Aptamers are oligonucleic acid or peptide molecules that bind to a specific target molecule. Aptamers are usually created by selecting them from a large random sequence pool, but natural aptamers also exist in riboswitches. Aptamers can be used for both basic research and clinical purposes as macromolecular drugs. More specifically, aptamers can be classified as DNA or RNA aptamers (consisting consist of (usually short) strands of oligonucleotides) and peptide aptamers (consisting of short variable peptide domain, attached at both ends to a protein scaffold). AptaBiD or Aptamer-Facilitated Biomarker Discovery is a technology for biomarker discovery. AptaBiD is based on multi-round generation of an aptamer or a pool of aptamers for differential molecular targets on the cells which facilitates exponential detection of biomarkers. The important feature of the AptaBiD technology is that it produces synthetic affinity probes (aptamers) simultaneously with biomarker discovery. In AptaBiD, aptamers are developed for cell surface biomarkers in their native state and conformation. In addition to facilitating biomarker identification, such aptamers can be directly used for cell isolation, cell visualization, and tracking cells in vivo.

Cell markers, also known as cell surface antigens, serve as monograms to help identify and classify cells. The majority of them are molecules or antigens within cell's plasma membrane. Unique to different cell types, there exist specific combinations of markers or antigens. These molecules serve not only as markers but they also have key functional roles. It is possible to diagnose diseases or direct treatment by identifying which molecules are present. Exemplary antibodies against cell markers or cell surface antigen include EB1 antibody, CNpase antibody, PDI antibody, celreticulin antiobody, lamin A+ antibody, fibrillarin antibody, Ki-67 antibody, cytochrome C antibody, c-fos antibody, EEA1 antibody and SCF antibody.

Exemplary antigens which may be used in combination with the respective antibody and which are specific for the indicated cell type include:

Neuronal Markers: Choline Acetyltransferase (ChAT) Glutamic Acid Decarboxylase-67 (GAD 67), Microtubule-Associated Protein (MAP2), Netrin, NF-H (Neurofilament 200 kDa), NF-L (Neurofilament Protein, 68 kDa), NF-M (Neurofilament 160 kDa), Neuron-Specific Enolase (NSE), Prostatic Acid Phosphatase (PAP), Synaptotagmin-1, TAU Tyrosine Hydroxylase (TYH) and Beta-Tubulin 3 (TUJ).

Glial and Schwann Cell Markers: Glial Fibrillary Acidic Protein (GFAP), CNPase (cyclic nucleotide phosphodiesterase), Coronin 1a, Myelin Basic Protein (MBP), Nestin, Proteolipid Protein (PLP), P-Zero Myelin Protein (Pz0) and Vimentin protein.

Endothelial Cell Markers: 7B4 antigen, ACE (angiotensin-converting enzyme), BNH9/BNF13, CD31, CD34, CD54 (ICAM-1), CD62P (p-Selectin GMP140), CD105 (Endoglin), CD146 (P1H12) and E-selectin.

Epithelial Cell Markers: F3, 4G10.3, A6 antigen, A33 antigen, adenosine 5'-triphosphatase, aminopeptidase N, APN/CD13, AUA1 and BerEP4 (Ber-EP4).

Further marker specific for particular cell types are available at http://www.antibodybeyond.com/reviews/cell-marker-reviews.htm.

Cytokines and growth factors are a category of signaling molecules active in cellular communication. They are proteins, peptides, or glycoproteins. Cytokines and growth factors are of vital importance to the development and functioning of both the innate and adaptive immune response. Cytokines and growth factors are often secreted by immune cells that have encountered a pathogen, thereby activating and recruiting further immune cells to enhance the system's response to the pathogen. Cytokines and growth factors are also involved in several developmental processes during embryogenesis. Exemplary antibodies include antibodies against IL-8, IP-10, M-.CSF, CT-1, SCF, BMP-7, FGF-6, FGF-16, RANTES and IL-1 beta.

The linker may be characterized in that it comprises
(i) a cleavage site for an enzyme;
(ii) a nucleic acid comprising a cleavage site for an enzyme;
(iii) a protein comprising a cleavage site for an enzyme;
(iv) a singlet oxygen-sensitive bond; or
(v) a pole sensitive to an electronically controllable charged group in the releaser.

The releaser may be characterized in that it is an enzyme, an apoenyzme, or a portion of a split enzyme, a photo sensitizer, an electronically controllable charged group targeting an opposite pole in the linker or a metal complex.

The releasing may be by cleaving the linker, particularly by
(i) enzyme-mediated cleaving of the linker;
(ii) photochemical, particularly singlet oxygen-mediated, cleaving of the linker;
(iii) chemical, particularly reductive, cleaving of the linker; or
(iv) electrochemical cleaving of the linker.

According to the present invention the solid support may be
(i) a bead, a vessel, a slide, a disk such as a compact disk or an array such as a microarray, and/or
(ii) glass, polystyrene, polyacrylamide, poly carbonate, polyethylene glycol (PEG), PEG-based or cellulose, optionally having a functionalized surface or being a chemically modified support, and/or
(iii) a petri dish, a microwell plate, a chromatography column, a chromatography matrix, a cell culture flask, a tube, a mesh or a membrane.

Further details on these specific embodiments are also given above or known to the skilled person.

In a further embodiments the method may comprise one or both of the following steps:
isolating the released one or more members of subgroup and/or
detecting the presence of one or more members of the subgroup.

With respect to definitions, specific embodiments and examples of the above features, it is referred to the details given in the context of the second and third method of the present invention.

The method of the present invention may be carried out in high-throughput format. The systems typically include robotic armature which transfers fluid from a source to a destination, a controller which controls the robotic armature, a data storage unit which records the detection, and an assay component such as a microtiter dish or a substrate comprising a fixed reactant. A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous polymerase reactions.

Another aspect of the present invention relates to method of detecting a subject's disease by detecting a sub-group of biological units indicative of the disease, the method comprising
  a) providing a heterogeneous group of biological units comprising a homogeneous subgroup of biological unity, the group of biological units being obtained from a subject and each member of the group of biological units being bound to an entity, preferably a solid support, via a linker; and
  b) contacting the group of biological units with a identifier, being capable of specifically binding the subgroup of biological units, under conditions allowing the binding of the identifier to the subgroup of biological units, wherein the identifier is coupled to a releaser, being capable of releasing the subgroup from the entity by interacting with the linker;
  c) binding the identifier to the subgroup, thereby bringing the releaser in proximity to the linker;
  d) specifically releasing one or more members of the subgroup from the entity by allowing interaction between the releaser and the linker; and
  e) detecting the presence of one or more members of the subgroup, thereby detecting the disease.

With respect to definitions, specific embodiments and examples of the above features, particularly of steps a) to d), it is referred to the details given in the context of the first method of the present invention.

In preferred embodiments of the present invention, the method of detecting a subject's disease by detecting a sub-group of biological units indicative of the disease is further defined as described above in the context of the method of specifically releasing a sub-group of objects from a solid support according to the present invention.

As detailed above, the group of biological units is obtained from a subject, e.g. from a subject's sample. "Sample" means a quantity of material that is suspected of containing one or more molecular complexes that are to be detected or measured. As used herein, the term includes a specimen (e.g., a biopsy or medical specimen) or a culture (e.g., microbiological culture). Samples may be animal, including human, fluid, solid (e.g., stool) or tissue. Samples may include materials taken from a patient including, but not limited to cultures, blood, saliva, cerebral spinal fluid, pleural fluid, milk, lymph, sputum, semen, needle aspirates, and the like. The sample may be obtained from all of the various families of domestic animals, as well as feral or wild animals, including, but not limited to, such animals as ungulates, bear, fish, rodents, etc. In regard to a human sample or "tissue sample" or "patient sample" or "patient cell or tissue sample" or "specimen," each means a collection of similar cells or biological or biochemical compounds obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like. The biological unit may be for example a cell or a part thereof, a cellular component such as a specific protein, nucleic acid, receptor, marker, metabolite, etc., a part of a tissue or organ, and the like.

The above method relates to a method of detecting a subject's disease by detecting a sub-group of biological units indicative of the disease. It is generally known that biological of a body (referred to as biological units) are indicative for diseases of that body. A multitude of examples is given above. Accordingly, the detection of these units (e.g. specific cells, protein, nucleic acids, small molecule compounds, etc.) is indicative of the disease. Methods of detecting biological units are well known in the art and include the following:

Mass spectrometry may be used. The term "mass spectrometry" refers to the use of an ionization source to generate gas phase ions from a sample on a surface and detecting the gas phase ions with a mass spectrometer. The term "laser desorption mass spectrometry" refers to the use of a laser as an ionization source to generate gas phase ions from a sample on a surface and detecting the gas phase ions with a mass spectrometer. A preferred method of mass spectrometry for biomolecules such as acylated acyl acceptor is matrix-assisted laser desorption/ionization mass spectrometry or MALDI. In MALDI, the analyte is typically mixed with a matrix material that, upon drying, co-crystallizes with the analyte. The matrix material absorbs energy from the energy source which otherwise would fragment the labile biomolecules or analytes. Another preferred method is surface-enhanced laser desorption/ionization mass spectrometry or SELDI. In SELDI, the surface on which the analyte is applied plays an active role in the analyte capture and/or desorption. In the context of the invention the sample comprises a biological sample that may have undergone chromatographic or other chemical processing and a suitable matrix substrate.

Suitable methods for detecting a protein include e.g. detection of a labeled protein (such as a fusion protein comprising a detectable marker, tag or enzyme component), protein immunostaining, protein immunoprecipitation, immunoelectrophoresis, immunoblotting, Western blotting, spectrophotometry, enzyme assays etc. The method may additionally require a further protein purification prior to the detection, which could involve protein isolation (e.g. by chromatography methods, protein extraction, protein solubilization, gel electrophoresis, and electrofocusing).

Suitable methods of detecting RNA include e.g. Northern blot analysis, nuclease protection assays (NPA), in situ hybridization, and reverse transcription-polymerase chain reaction (RT-PCR).

Suitable methods of detecting DNA include e.g. Cycling probe technology, Tunel, Southern blot analysis, autoradiography, electrophoresis, methods involving the use of autoradiography, silver staining, ethidium bromide, SYBR green, fluorescent dyes, labeled DNA binding partners etc.

Another aspect of the present invention relaters to a method of isolating one or more members of a sub-group of objects from a group of objects, the method comprising
  a) providing a heterogeneous group of objects comprising a homogeneous subgroup of objects, each member of the group of objects being bound to an entity, preferably a solid support, via a linker; and
  b) contacting the group of objects with a identifier, being capable of specifically binding the subgroup of objects, under conditions allowing the binding of the identifier to the subgroup of objects, wherein the identifier is coupled to a releaser being capable of releasing the subgroup from the entity by interacting with the linker;
  c) binding the identifier to one or more members of the subgroup, thereby bringing the releaser in proximity to the linker;
  d) specifically releasing one or more members of the subgroup from the entity by allowing interaction between the releaser and the linker; and
  e) isolating the released one or more members of subgroup.

With respect to definitions, specific embodiments and examples of the above features, particularly of steps a) to d), it is referred to the details given in the context of the first and second method of the present invention.

In preferred embodiments of the present invention, the method of isolating a sub-group of objects from a group of objects is further defined as described above in the context of the method of specifically releasing a sub-group of objects from a solid support according to the present invention.

The above method relates to a method of isolating one or more members of a sub-group of objects from a group of objects. The method of steps a) to d) is suitable for the specific release of a binding partner to an identifier. This method may be used in the identification of the identification of unknown binding partners or for the isolation of known binding partner. Due to the specific release the binding partner to the identifier is isolated from other members of the groups and the other members may be removed from the binding partner to the identifier based on the specific release (as detailed above). For example, the binding partner may be released from a solid support and the unreleased members of the group may be removed by removing the solid support. Additional isolation steps as known to the skilled person may be added.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The following Figures and Examples are intended to illustrate various embodiments of the invention. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

The invention claimed is:

1. A method of specifically releasing one or more members of a sub-group of objects from an entity, the method comprising
  a) providing a heterogeneous group of objects comprising a homogeneous subgroup of objects, each member of the group of objects being bound to the entity via a linker;
  b) contacting the group of objects with an identifier, being capable of specifically binding the subgroup of objects, under conditions allowing the binding of the identifier to the subgroup of objects, wherein the identifier is coupled to a releaser being capable of releasing a member of the subgroup from the entity by interacting with the linker;
  c) binding the identifier to the subgroup, thereby bringing the releaser in proximity to the linker; and
  d) specifically releasing one or more members of the subgroup from the entity by allowing interaction between releaser and linker;
  thereby specifically releasing the one or more members of the subgroup of objects from the entity.

2. The method of claim 1, wherein the entity is a support, particularly a solid support.

3. The method of claim 1, wherein the objects are proteins, nucleic acids, antigens, antibodies or functionally active derivatives thereof.

4. The method of claim 1, wherein the heterogeneous group of objects comprising a homogeneous subgroup of objects is a heterogeneous population of cells comprising a homogeneous sub-population of cells.

5. The method of claim 4, wherein
  a) the sub-population of cells consists of rare cells, particularly wherein in the population the ratio of rare cells to total cells is at most 5%, preferably at most 1%, especially at most 0.1%, such as at most 0.01%; or
  b) in the population the ratio of cells of the homogeneous sub-population of cells to total cells is at most 50%, especially in the range from 5% to 50%, particularly in the range from 10% to 30%.

6. The method of claim 4, wherein the sub-population of cells is
  indicative of a disease, particularly of cancer; or
  composed of cells of one cell type.

7. The method of claim 1, wherein the identifier is selected from the group comprising a protein, a nucleic acid, an antibody or functionally active derivative thereof, a receptor or a binding site thereof, an enzyme or a binding site thereof, a tag-binding site, a ligand to a receptor, a substrate to an enzyme or a tag.

8. The method of claim 1, wherein the linker comprises
  (i) a cleavage site for an enzyme;
  (ii) a nucleic acid comprising a cleavage site for an enzyme;
  (iii) a protein comprising a cleavage site for an enzyme;
  (iv) a singlet oxygen-sensitive bond; or
  (v) a pole sensitive to an electronically controllable charged group in the releaser.

9. The method of claim 1, wherein the releaser is an enzyme, an apoenyzme, or a portion of a split enzyme, a photo sensitizer, an electronically controllable charged group targeting an opposite pole in the linker or a metal complex.

10. The method of claim 1, wherein the releasing is by cleaving the linker, particularly by
   (i) enzyme-mediated cleaving of the linker;
   (ii) photochemical, particularly singlet oxygen-mediated, cleaving of the linker;
   (iii) chemical, particularly reductive, cleaving of the linker; or
   (iv) electrochemical cleaving of the linker.

11. The method of claim 2, wherein the solid support is
   (i) a bead, a vessel, a slide, a disk such as a compact disk or an array such as a microarray, and/or
   (ii) glass, polystyrene, polyacrylamide, poly carbonate, polyethylene glycol (PEG), PEG-based or cellulose, optionally having a functionalized surface or being a chemically modified support, and/or
   (iii) a petri dish, a microwell plate, a chromatography column, a chromatography matrix, a cell culture flask, a tube, a mesh or a membrane.

12. A method of detecting a subject's disease by detecting a sub-group of biological units indicative of the disease, the method comprising
   a) providing a heterogeneous group of biological units comprising a homogeneous subgroup of biological unity, the group of biological units being obtained from a subject and each member of the group of biological units being bound to an entity, preferably a solid support, via a linker; and
   b) contacting the group of biological units with a identifier, being capable of specifically binding the subgroup of biological units, under conditions allowing the binding of the identifier to the subgroup of biological units, wherein the identifier is coupled to a releaser, being capable of releasing the subgroup from the entity by interacting with the linker;
   c) binding the identifier to the subgroup, thereby bringing the releaser in proximity to the linker;
   d) specifically releasing one or more members of the subgroup from the entity by allowing interaction between the releaser and the linker; and
   e) detecting the presence of one or more members of the subgroup, thereby detecting the disease.

13. A method of isolating one or more members of a sub-group of objects from a group of objects, the method comprising
   a) providing a heterogeneous group of objects comprising a homogeneous subgroup of objects, each member of the group of objects being bound to an entity, preferably a solid support, via a linker; and
   b) contacting the group of objects with a identifier, being capable of specifically binding the subgroup of objects, under conditions allowing the binding of the identifier to the subgroup of objects, wherein the identifier is coupled to a releaser being capable of releasing the subgroup from the entity by interacting with the linker;
   c) binding the identifier to one or more members of the subgroup, thereby bringing the releaser in proximity to the linker;
   d) specifically releasing one or more members of the subgroup from the entity by allowing interaction between the releaser and the linker; and
   e) isolating the released one or more members of the subgroup.

* * * * *